United States Patent [19]

Landh et al.

[11] Patent Number: 5,531,925

[45] Date of Patent: Jul. 2, 1996

[54] PARTICLES, METHOD OF PREPARING SAID PARTICLES AND USES THEREOF

[75] Inventors: Tomas Landh, Lund; Kåre Larsson, Bjärred, both of Sweden

[73] Assignee: GS Biochem AB, Malmo, Sweden

[21] Appl. No.: 211,293

[22] PCT Filed: Oct. 2, 1992

[86] PCT No.: PCT/SE92/00692

§ 371 Date: Apr. 11, 1994

§ 102(e) Date: Apr. 11, 1994

[87] PCT Pub. No.: WO93/06921

PCT Pub. Date: Apr. 15, 1993

[51] Int. Cl.[6] ............... C09K 19/00; A61K 9/66; B01J 13/00

[52] U.S. Cl. .............. 252/299.01; 428/1; 428/402; 424/450; 424/455; 252/302; 514/937; 514/964

[58] Field of Search .............. 252/299.01; 428/302–402; 514/937, 964; 424/455, 450

[56] References Cited

U.S. PATENT DOCUMENTS

| | | | |
|---|---|---|---|
| 4,556,289 | 12/1985 | Ferguson | 359/51 |
| 5,021,195 | 6/1991 | Machin et al. | 252/545 |
| 5,030,452 | 7/1991 | Curatolo | 424/450 |
| 5,108,756 | 4/1992 | Curatolo | 424/450 |
| 5,143,934 | 9/1992 | Lading et al. | 514/396 |
| 5,151,272 | 9/1992 | Engström et al. | 424/450 |
| 5,371,109 | 12/1994 | Engström et al. | 514/786 |

FOREIGN PATENT DOCUMENTS

| | | |
|---|---|---|
| 0119867 | 9/1984 | European Pat. Off. |
| 0378403 | 7/1990 | European Pat. Off. |
| 03139525A | 6/1991 | Japan |
| WO84/02076 | 6/1984 | WIPO |

OTHER PUBLICATIONS

"Drug Delivery from Cubic and Other Lipid–Water Phases", Sven Engström, Lipid Technology, vol. 2, No. 2, pp. 42–45 (Apr. 1990).

*Primary Examiner*—Shean C. Wu
*Attorney, Agent, or Firm*—Burns, Doane, Swecker & Mathis

[57] ABSTRACT

Particles, especially colloidal particles, comprising an interior phase of a non-lamellar reversed cubic, intermediate or hexagonal liquid crystalline phase, or a homogeneous L3 phase, and a surface phase of a lamellar crystalline or liquid crystalline phase, or an L3 phase. A method of preparing such particles by creating a local dispersible phase, within the homogeneous phase, preferably by means of a fragmentation agent, and fragmentating the homogeneous phase so as to form said surface phase. Several medical as well as non-medical uses of the particles referred to, e.g. as an antigen-presenting system, as a delivery system for anticancer, antifungal and antimicrobial drugs, and as carriers of nucleic acids or nucleotides.

35 Claims, No Drawings

5,531,925

PARTICLES, METHOD OF PREPARING SAID PARTICLES AND USES THEREOF

This is a application of PCT/SE92/00692 filed under 35 USC 371, which is a continuation of U.S. application Ser. No. 07/771,014 now abandoned.

1. FIELD OF THE INVENTION

The present invention relates to the field of amphiphilic-solvent based systems and more specifically To the fragmentation of such systems by means of a novel method. Thus, by means of said novel method systems, which are otherwise homogeneous and in equilibrum, can be fragmented into small particles, especially colloidal particles. These new particles are extremely well suited as e.g. drug delivery particles or systems, but are also useful for several other medical as well as non-medical applications. Thus, the invention also encompasses said new particles as well as valuable uses thereof.

2. BACKGROUND OF THE INVENTION

The use of reversed cubic and liquid crystalline phases in the field of controlled release devices is described in EPO 125 751 (Engström et al 1983). However, there are many applications where the use of a homogeneous phase is not manageable. By the present invention it has become possible to prepare particles, especially colloidal particles, of such phases or similar phases, viz by means of a new fragmentation technique. The importance of said new technique, and the new particles obtained thereby, can be better understood from the following brief review of the prior art concerning other Types of particles and homogeneous phases.

2.1. Dispersed lipid-based systems in pharmaceutical preparations

Essentially, there have To date been three major particulate colloidal lipid-water systems which have been considered as suitable for drug delivery, namely such based on the lamellar mesophase as liposomes, micellar-based phases including micelles, reversed micelles, and mixed micelles and various kinds of emulsions including microemulsions, as well as more novel carriers as ISCOM's (Morein 1988) (a general text concerning these systems is Pharmaceutical dosage forms, Disperse systems 1988). The latter system has been utilized for intravenous nutrition since the beginning of this century and as an adjuvant system known as the Freunds adjuvant. These are of oil-in-water (O/W) and water-in-oil (W/O) types, respectively. Liposomes have since their discovery been extensively investigated as drug delivery systems for various routes and drugs. The development of new colloidal drug carrier systems is a research area of intensive activity and it is likely that new systems, especially new emulsion based systems, will appear in the near future (cf. Weiner 1990a, 1990b). Lipid-based vehicles can take several different morphological forms such as normal and reversed micelles, microemulsions, liposomes including variants as unilamellar, multilamellar, etc., emulsions including various types as oil-in-water, water-in-oil, multiple emulsions, etc., suspensions, and solid crystalline. In addition so called niosomes formed from nonionic surfactants have been investigated as a drug vehicle. The use of these vehicles in the field of drug delivery and biotechnology is well documented (Mulley 1974, Davis et al. 1983, Gregoriadis 1988a, Liebermann et al 1989). Particularly in the field of drug delivery the use of lipid-based drug delivery systems, especially dispersed systems, has attained increasing interest as the pharmaceutical industry is developing more potent and specific—and thus more (cyto)toxic—drugs. This is because the vehicle can in principle reduce such toxic effects and/or side-effects, due to sustained release or increased site-specificity. The current invention is easily distinguished from these earlier lipid-water based systems, as follows:

The term liposomes is conceptually wrong in view of the current knowledge of polymorphism of lipids. Liposome means "lipid body" and has by many authorities in the field been defined as any structure with an enclosed volume that is composed of lipid bilayers (see eg. Tice and Tabibi 1992). This is not only very misleading but also conceptually wrong. Such a definition means that any dispersed lipid based structure built up by a bilayer should fall into this category of device without regarding the different crystallographic aspect of the undispersed, homogeneous, phase from which the particulate vehicle is derived. It would, however, not include dispersions in which the interior of the particles is made up by reversed hexagonal phases, since they are built up by a monolayer, rather than a bilayer. Unfortunately, the concepts of lipid polymorphism and in particular the more complex structures of cubic liquid crystalline phases are often overlooked. Since the current disclosure is in the field of lipid-based vehicles, in which various reversed lyotropic liquid crystalline phases are enclosed in a volume whose boundary is made up by L3 phase or lamellar crystalline phase or lamellar liquid crystalline phase, or a combination thereof, it should be stressed that the current invention encloses either lipid bilayer or monolayer structures different from the lamellar phase. The ordered interior of each particle in the current invention is a portion of a lipid-water microstructured phase that is a thermodynamically stable phase, either a cubic, hexagonal, intermediate phase or an L3 phase. The L3 phase is not classified as a liquid crystalline phase, as the others, rather it is an isotropic solution phase, using the standard nomenclature in the literature of amphiphile microstructures. The physical properties of the homogeneous reversed liquid crystalline phases used in the currect disclosure are those presented in the patent by Engström et al. (1983) referred to. In the cases where a cubic phase constitutes the interior of the particles it is built up by a bi- or multicontinuous interpenetrating network microstructure, at the scale of nanometers. This makes these phases unique with regard to compartmentalization since the two independent interpenetrating networks separated by the bilayer can be distinguished, and endows them with extremely high specific surface area, which is especially important in the formulation of amphiphilic drugs straddle hydrophobic and hydrophilic microdomains.

The current invention is thus easily and sharply distinguished from both liposomes, emulsions, microemulsions, as well as various microencapsulated emulsions, hydrogels, and reversed micelles. Most obviously, the interior phase(s) of the current particles is (are) a thermodynamic equilibrium phase, and thus appears as a discrete region in a phase diagram which obeys the phase rule of Gibb's and other laws of chemical and thermodynamical equilibria; this is in sharp contrast with liposomes and emulsions, which are non-equilibrium states or morphologies. [Note that we are using the convention of referring to equilibrium structures as "phases" and non-equilibrium structures as "states"]. In the case of emulsions the interior is also thermodynamical stable, but it is an interior which lacks long-range order, and is not composed of either lipid bilayers or lipid monolayers, or analogous structural elements. This is a clear distinction, which is directly accessible to experiment, since the interior phase used in the current particles give rise to Bragg peaks on examination with small-angle X-ray (or neutron) scattering techniques, in accordance with its lattice ordering; thus the Bragg peaks recorded can be indexed to e.g. a simple cubic, body-centered cubic, or face-centered cubic lattice, hexagonal lattice, or tetragonal lattice in the case the interior is made up by a cubic phase, a hexagonal phase or intermediate tetragonal phase, respectively. In contrast, no case has ever been reported in which multiple Bragg peaks, indexing to any of these lattices, were recorded in a small-angle scattering experiment on a liposomal dispersion or an emulsion. Clearly, the surface of the current particles can in practice give rise to diffraction indexing on a lamellar lattice. In the case of microemulsions and reversed micellar phase, both lacking long range order, they are clearly distinguished from the L3 phases in the current surfactant literature.

The distinctions between the current invention on the one hand, and the liposomal dispersions and emulsions on the other, then follow directly from the above distinctions, and it is only in the case of the reversed liquid crystalline phase dispersions disclosed herein the interiors of the particles are substantially composed of regions of reversed liquid crystalline phase(s).

In the case of dispersions of L3 phases, the interiors of the particles are not composed of liquid crystalline material but of the to the cubic phases closely related L3 phases. The L3 phases are thermodynamic equilibrium phases, distinguishing them from liposomes and emulsions as in the case of cubic phases. The lipid film forms a highly connected bilayer as in the cubic phase, again in contrast with the liposomes and emulsions. However, in this case scattering experiments do not reveal long-range order as in the cubic phase.

Of special importance in formulations, used either for drug delivery or for biological or biotechnological applications, is the position and orientation of the compound with respect to the bilayer. In the current invention specific orientation may be readily achieved in the case the interior is composed of cubic phase, for which it is an inherent property, as opposed to liposomal bilyaers. This substantially simplifies the process of standardizing enzyme activity in the formulation. Such selectivity in membrane topography is not easily established in other lipid-based systems such as liposomes and emulsions. There are several other areas of interest where the presented topography of the compound is of profound importance, as with antigen presentation in immunization processes. The current invention can accomplish the optimization of this presentation for both extracellular and intracellular targets.

2.2. Homogeneous liquid crystalline phases in pharmaceutical preparations

Liquid crystals do participate in the microstructure of pharmaceutical preparations, and probably do so more frequently than is usually expected. The use of homogeneous reversed cubic and hexagonal phases as a controlled release system for use in e.g. drug delivery systems was invented by Engström, Larsson, and Lindman in Lund, Sweden, who are holders of a current patent (Engström et al. 1983, see also Ericsson et al 1991, and references therein). Dr. D. Attwood and coworkers in Manchester, UK, have also investigated the use of cubic phases for the purpose of drug delivery (cf. Burrows et al 1990).

Cf. also Mueller-Goymann and collaborators (Mueller-Goymann 1985, Mueller-Goymann 1987, Mueller-Goymann 1989 and references within these works). Other contributions occur in the literature (cf. Ibrahim 1989, Tyle 1990) and are not restricted to lyotropic liquid crystals (Loth and Euschen 1990).

2.3. Dispersed reversed cubic liquid crystalline phases

There have been speculations of the existance of dispersed cubic liquid crystalline phases in connection with fat digestion (cf. Lindström et al 1981) and recently Larsson (1989) suggested a structure of such cubic phase dispersions; in these, the surface layer was proposed to be a lamellar phase, which immediately distinguishes such dispersions from the particles whose surface phase is L3 phase disclosed herein—the particles in this embodiment of the present invention are isotropic throughout, whereas those discussed by Larsson (1989) contain anisotropic, birefringent regions which are easily detected in the polarizing microscope. The only exception is particles, described in the present disclosure, which are surrounded by a lipid structure which is crystalline, not liquid crystalline as in the lamellar phase. Regarding the case of dispersions of reversed liquid crystalline phases by the use of a lamellar liquid crystalline phase as a dispersable phase the novel fragmentation technique according to the invention can be used.

2.4. Phase behavior in lipid-water based systems and the determination of cubic phases A "lipid" is, in a broad view, defined as any molecule containing a substantial part of hydrocarbon. However, only those lipids that contain a hydrophilic polar part can give rise to liquid crystals by interactions with water. The basis for lipid lyotropic (and thermotropic) mesomorphism, and the formation of lipid assemblies, is the duality in solubility resulting from the presence of apolar (hydrophobic) and polar (generally hydrophilic) regions of the surfactant molecule—that is, its amphiphilicity (or amphipaticity). Amphiphilic lipids can be classified according to their interactions with water into nonpolar and polar (Small 1986). Where applicable within this disclosure we are concerned with lipids or lipid-like amphiphiles that exhibit mesomorphism and are thus classified as polar, insoluble and swelling amphiphiles. If nothing else is said we use the terminology introduced by Luzzati and associates (see Mariani et al. 1988, and ref. therein).

The principal techniques for studying the different phase structures are polarizing microscopy, X-ray diffraction, nuclear magnetic resonance (NMR) spectroscopy and electron microscopy techniques. Other techniques, as differential scanning calorimetry (DSC) and rheology can be used to give complementary information. Unambiguously phase determinations of the phases constituting the interior as well as the exterior is a prerequisite in order to classify dispersions according to the current invention. Preliminary phase behavior is usually carried out by texture analysis between crossed polarizers and more detailed in a polarizing microscope (Rosevear 1968). X-ray diffraction techniques are the obvious methods to deduce the symmetry of liquid crystals. The characterization of lipid mesophases by diffraction (Luzzati 1968) is based firstly on symmetry and the interpretation is normally based on treating the diffraction photographs as powder patterns. The long-range order of the assemblies in either one, two, or three dimensions, give rise to reflections which are converted to interplanar spacings. It is only with X-ray diffraction studies phase assignments can be regarded as unambiguous.

2.4.1. Phase diagrams in lipid-water systems

Fontell (1990) gives a comprehensive and systematic reveiw on cubic phase forming lipids and lipid-like surfactants and the occurrence of the cubic phases in the phase diagram and their relation to other phases. The information obtained from the structure of the neighboring phases can often be valuable for the identification of a cubic phase. The fact that a mesophase, such as the cubic or hexagonal phase, is in equilibrium with excess of water, is itself a strong indication that the structure is of the reversed, type II topology.

In the context of this invention, two examples of lipid-water based systems have been investigated with the objective of mapping the underlying phase behavior so as to understand and develop the techniques disclosed herein regarding the fragmentation process: Commercially available products have been used throughout this study, and it is important to note that these are generally not single-component products. We first discuss the binary phase diagram of the glycerol monooleate (GMO)-water system. The GMO has been obtained through molecular distillation of pine-needle oil (Grinsted, Denmark), and has a monoglyceride content of >98%, of which 92.3% is monoolein (MO) (MO refers to the pure monoolein, while GMO refers to a monoolein rich monoglyceride blend). Many phase diagrams have been reported involving cubic phases of monoglycerides (Lutton (1965), Larsson et al. 1978, Krog and Larsson 1983, Larsson 1989, Krog 1990). In addition to the pure lipids monoolein, monoelaidin, monolinolein, monoarachidin, and monolinolein (Lutton 1965, Larsson et al. 1978, Hyde et al. 1984, Caffrey 1989), several blend qualities of monoacylglycerides are well characterized and known to form cubic phases in equilibrium with water (Larsson and Krog 1983, Krog 1990). Significantly, these blends are available at low production costs, typically less than $2 per pound.

Monoacylglycerides are often used in cosmetic products (Cosmetic Ingredient Review expert panel 1986), food industry (Krogh 1990) and pharmaceutics (Martindale the extra pharmacopoeia 1982), and are generally recognized as safe (GRAS) substances and as indirect food additives for human consumption without restrictions as to their concentrations. Federal regulations allow the use of monoglycerides, blends thereof, and blends of mono- and diglycerides as prior-sanctioned food ingredients and as both indirect and direct food additives. Furthermore, the metabolic fate of monoglycerides (and glycerides in general) is well documented in the human body. In the cosmetic industry monoglycerides and blends thereof, especially monoolein, are used as emulsifiers and thickening agents and recognized as safe cosmetic ingredients at concentrations up to 5% (Cosmetic Ingredient Review expert panel 1986).

The fact that there exists cubic phases in equilibrium with excess of water in the above mentioned monoglyceride systems is a strong indication that the cubic phase is of the reversed, type II topology. This has been verified by self-diffusion NMR (Lindblom et al. 1979). It should be pointed out that several systems which form cubic phases of the reversed type exhibit cubic mesomorphism, i.e. the appearance of a sequence of distinguishable cubic phases with different physical appearance, as well as exhibiting different lattice characteristics. The phase behavior of the present GMO-water system was; found to be very similar to that of MO-water reported by Hyde et al. (1984) (Engström and Engström 1992). The $Q^{224}$ was found to be the cubic phase which coexists with excess of water.

The second lipid-water system used is the ternary system of GMO-soybean lecithin (SPC)-water. SPC is a pure phosphatidylcholine with the trade name Epikuron 200 which is well-characterized (Bergenståhl and Fontell 1983). It shares the general features of the phase diagram for MO-dioleoyl phosphatidylcholine-heavy water system reported by Gutman et al (1984). The existence of three cubic phases within the cubic region is experimentally verified by X-ray diffraction, as was the coexistence of cubic phases with excess of water.

2.4.2. Phase behavior and phase diagrams in lipid-protein-water systems

The phase properties in lipid-protein-water mixtures is a relatively unexplored area of research. Most of the studies have been reported by the Groups of Gulik-Krzywicki, Luzzati and colleagues (cf. Mariani et al. 1988, Gulik-Krzywicki 1975), by De Kruijff and coworkers (cf. Killian and De Kruijff 1986) and by Larsson and coworkers (cf. Ericsson et al. 1983, Ericsson 1986). Most studies address the behavior in diluted systems and often deal with the stability of the lamellar phase vs. the reversed hexagonal phase. The induction of non-lamellar phases is well established-for quite many systems. Some works address the phase properties vs. the activity of membrane bound enzymes, and it has been possible in some works to establish a correlation between an increased enzyme activity and isotropic movement of the lipid matrix. In the field of enzyme catalysis in microemulsions, some studies deal with the phase behavior; however, few works present phase diagrams.

That the cubic phases in the monoolein (MO)-water system could host quite large amounts of various substances, included proteins, had been known for many years (cf. Lindblom et al. 1979). The phase diagram of MO-lysozyme-water displays the general features of MO-protein-water systems, in cases where the protein is located in the aqueous labyrinths of the cubic phase (Ericsson et al. 1983). Ericsson (1986) reported a considerable number of proteins which can be incorporated within the MO-water cubic phase.

The second system which has been investigates in considerable detail is the MO-cytochrome c-water system reported by Luzzati and coworkers (Mariani et al. 1988), and it exhibits the general features found in the MO-lysozyme-water system. However, it also shows some features which necessary must arise from the protein; noteworthy is the existence of a chiral, non-centrosymmetric cubic phase, with space group 212. These aqueous MO-protein systems all exhibit at least one cubic phase which fulfils the criteria for constituting the interior phase of the particles according to the present invention.

2.5 Structure of the interior phases

The interior of the particles according to the invention consists of reversed lyotropic liquid crystalline phases, chosen from the group of reversed cubic liquid crystalline phases, reversed intermediate liquid crystalline phase, and reversed hexagonal liquid crystalline phase, or L3 phase, or a combination thereof. These phases are all well characterized and well established in the field of polymorphism of lipids and surfactants.

2.5.1. Structure of the cubic and hexagonal phases

Several reviews are available where cubic phases are discussed; see e.g. Luzzati (1968), Fontell (1974, 1978, 1981), Ekwall (1975), Tiddy (1980) and Luzzati et al. (1986). In recent years several surveys devoted to cubic phases have appeared. Luzzati and associates (Mariani et al. 1988) (see also Luzzati et al. 1987) give a detailed crystallographic description of the current situation with regard to the structure of the six cubic phases observed so far. Lindblom and Rilfors (1988) have reviewed the occurrence and biological implications of cubic phases formed by membrane lipids, and Larsson (1989) has reviewed the latest developments in the study of cubic lipid-water phases. A comprehensive review of the occurrence of cubic phases in literature phase diagrams was recently presented by Fontell (1990).

A general classification of the cubic phases is still not available. However, in the case of bilayer-bicontinuous cubic phases in binary systems they can be classified according to their interfacial mean curvature as "normal" (type I) or reversed (type II) cubic phases. Type cubic phases are those whose mean curvature at the apolar/polar interface is toward the apolar regions. Contrarily, type II or reversed cubic phases are those whose interface is towards the polar regions. In connection with the invention we are only concerned with cubic phases of type II, i.e. reversed.

Regarding the structure of the hexagonal phase it consists of hexagonally arranged rods of water (solvent) surrounded by a monolayer of amphiphile (see e.g. Seddon 1990, for a review).

2.5.2. Structure of the L3 phase

The microstructures of the L3 phases referred to are similar to those frequently found in surfactant-water systems (Benton et al. 1983, Porte et al. 1988, Gazeau et al. 1989, Anderson et al. 1989, Strey et al. 1990a, Strey et al. 1990b, Milner et al. 1990). The acquiescent L3 phase is isotropic. However, one striking and characteristic feature is that it shows extended flow birefringence. Other characteristics include long equilibration times and, at least relative to the amphiphile concentration, high viscosity. The structure is generally believed to be built up of multiply-connected bilayer forming a bicontinuous structure of high connectivity, and it may be regarded as a disordered counterpart to the cubic phases (Anderson et al. 1989), possessing similar topological connectivity and a local bilayer structure, but lacking long-range order.

2.6. Structure of the surface or dispersable phases

The structure of the L3 phase when used as the dispersable or fragmenting phase is exactly as described in 2.5.2. It should be pointed out that one bilayer of an L3 phase can not readily be distinguished from a lamella of a diluted lamellar phase. Similarly, it has been pointed out that the L3 phase may in certain systems exhibit metastability (Dubois and Zemb 1991) in which a transformation of the L3 phase to a lamellar phase was observed after 3 weeks of equilibration time. The lamellar structures, including lamellar phases with: disordered chains, untilted ordered or gel, and tilted gel, used as the dispersable phases are described by Luzzati (1968).

3. DISCLOSURE OF THE INVENTION

The present invention relates to new particles, especially colloidal particles, made from reversed cubic, hexagonal or intermediate phases, or L3 phases, or mixtures thereof, by fragmentation of the corresponding homogeneous structure. Fragmentation can be achieved through several processes described below. The resulting particles are thus composed of an interior amphiphilic-based phase surrounded by a surface phase anchored to the bi- or mono-layer of the interior phase. The properties of the surface phase is such that it can easily be dispersed.

Thus, the present invention is in the field of lipid-based dispersed vehicles representing novel drug delivery systems. The invention is nonetheless sharply distinguished from liposomes and emulsions, and similar particulate vehicles as well as from the techniques used for the preparation of such lipid-based particulate systems. The class of delivery vehicles claimed comprises particles whose interiors are substantially composed of lyotropic liquid crystalline phases of bilayer or monolayer type, or the closely related L3 phases which lack long-range super-molecular order; the reversed lyotropic liquid crystalline phases can be chosen from the group consisting of The cubic phase, the hexagonal phase, and the intermediate phase, or a combination thereof, using the nomenclature in the current surfactant literature. These liquid crystals are thermodynamic equilibrium phases, in contrast with liposomes and emulsions which are metastable. With the interior of The current particles being liquid crystals, they exhibit Bragg peaks in small-angle X-ray scattering (SAXS) experiments, as opposed to liposomes and emulsions which do not possess long-range crystallographic order on the microstructural length scale, namely lattice parameters in the range of nanometers or more. Dispersions of the liquid crystals loaded with an active compound can be conveniently prepared by fragmentation of the homogeneous liquid crystal. A variety of techniques disclosed herein can be used for The fragmentation process, creating different surface properties of the particles, depending on the choice of dispersable phase and its composition. The fragmentation can be spontaneous or aided by standard homogenizing means such as valve homogenizers. The dispersions can display long-term stability.

More specifically The new particles according to the invention comprise an interior phase of a non-lamellar lyotropic liquid crystalline phase selected from the group consisting of a reversed cubic liquid crystalline phase, a reversed intermediate liquid crystalline phase and a reversed hexagonal liquid crystalline phase, or a homogeneous L3 phase, or any combination thereof, and a surface phase selected from the group consisting of a lamellar crystalline phase and a lamellar liquid crystalline phase, or an L3 phase, or any combination thereof.

Thus, the invention makes use of non-lamellar, but equilibrium, reversed lyotropic liquid crystalline phases that occur in many lipid-water and other amphiphile-solvent based systems. The following terminology is used: The particles whose inner is made up by non-lammelar phases, the interior phase, are prepared by a novel fragmentation procedure which makes use of the introduction of disclinations/defects in the interior phase by the local formation of a dispersable phase such as the L3 phase, lamellar liquid crystalline phase, or lamellar crystalline phase, or a combination thereof. The so formed disclinations, whose boundaries make up the dispersable phase referred to as the surface phase of the particles, in turn constitute the boundary of a fragment of the interior phase of the particles. The fragmentation procedure takes place in such a way that it guarantees the coexistence of the phase making up the interior, the phase making up the surface, and the solvent-rich solution phase. The latter is most often rich in water, or any other polar solvent, or solvent in which the interior phase(s) of the particles is (are) formed. A three phase region can hence be determined as the region of which these phases coexist and in which the interior phase is fragmented according to above. The particle size can thus be varied to a certain extent since the amount of dispersable phase will determine the maximum sum of surface area of the particles. The invention makes use of phases constituting the interior phase chosen from the group of reversed cubic liquid crystalline phases, reversed hexagonal liquid crystalline phase, and reversed intermediate liquid crystalline phase, or a combination thereof, or an L3 phase. It is in fact a prerequisite that when the interior phase is a liquid crystalline phase it is of reversed type since it must be able to coexist with the solvent-rich phase.

More specifically the method according to the invention comprises forming a homogeneous, non-lamellar lyotropic liquid crystalline phase selected from the group consisting of a reversed cubic liquid crystalline phase, a reversed intermediate liquid crystalline phase and a reversed hexagonal liquid crystalline phase, or a homogeneous L3 phase, or any combination thereof, creating a local dispersible phase, within said homogeneous phase, of a phase selected from the group consisting of a lamellar crystalline phase and a lamellar liquid crystalline phase, or an L3 phase, or any combination thereof, in the presence of a solvent phase, said solvent being of a nature with which said homogeneous phase can coexist and wherein said dispersible phase can be dispersed, and fragmentating said homogeneous phase so as to form particles, the interior phase of which comprises said homogeneous phase and the surface phase of which comprises said dispersible phase.

Generally, a fragmentation agent is used to establish the final appearance of the interior phase as well as the surface phase, even though it may only be a change in lattice parameter of the interior phase, or the establishment of a new interior phase not present in the system lacking the fragmentation agent.

The structure of the surface phase can vary depending on the preparation of the particles to be either diluted lamellae (lamellar liquid crystalline phase), lamellar crystalline phase, or an L3 phase. The colloidal fragmented L3 phase particles are made from cubic phases through lyotropic phase transformation of the dispersed cubic phase. Alternative formulations resulting in substantially the same final microstructure for the dispersion fall within the scope of this invention.

Especially preferable embodiments of the particles as well as the method according to the invention show those characteristic features which are claimed in the accompanying claims. These embodiments as well as other embodiments of the invention will now be described more in detail.

3.1. Dispersions of reversed liquid crystalline phases

A convenient starting point for the formation of cubic phase dispersions is a cubic phase that can be in thermodynamic equilibrium with excess of water or aqueous (molecular or dilute micellar-like) solution. We describe only the invention exemplified in detail with the case of cubic phase interior, since exactly the same procedure can be applied to sytems possessing a reversed hexagonal or intermediate phase in excess of water. Several systems in which a cubic phase coexists with a very diluted ,aqueous solution have been described in the literature (for a review, see Fontell 1990), all of which can in principle be applied to the current invention. Many monoacylglyceride-water systems possess this feature (see 2.4.) and are suitable to exemplify the invention.

MO may be considered as a fusogenic lipid and can generally not be regarded as blood compatible, at least not as a monomer or as assembled in the cubic phase. However, the particles claimed are blood compatible (with the exception of the dispersion with a crystalline outer palisade, discussed below) as indicated by the lack of lysis products after incubation with red blood cells for 1 hr. This may be attributed to the very hydrophilic palisade layer constituted by the surface phase, surrounding the particles. The surface phase can conveniently be chosen to be composed of polyethylenoxide units or glyco- moieties, or a mixture of these. In these cases, the palisade to some extent mimics the glycocalyx of blood cells. The chemical constituents of the cubic phase can further be varied by exchanging the monoglycerides by phospholipids such as soybean lecithin, egg yolk lecithin, pure phospholipids as dioleoylphosphatidylcholine, and diglycerides. By such means, the molecular constituents of the bilayer structure can be systematically varied so as to achieve the desired properties as described in detail below.

Solubilized (active) component(s) also play a role in the final properties of the formulation, especially if large amounts of active substance are incorporated. To date, every compound which has been solubilized in the aqueous networks of a reversed cubic phase has been found to increase in solubility in comparison with that in aqueous solution. This has been found to be particularly pronounced in cases where the amphiphilic character of the compound calls for the unique, amphiphilic compartmentalization afforded by the cubic phase, so that both solubility and stability are increased in the cubic phase. Such compounds are e.g. global proteins and glycoproteins, polynucleotides and highly reactive lipids as prostaglandins and their derivatives as thromboxanes. We strongly emphasize that the current invention is applicable to any reversed liquid crystalline phase defined as the interior, and to any of the defined surface phases, and their coexistence in any Type of solvent-rich media (solution phase) regardless of their molecular composition. The formulation of different molecules in the reversed liquid crystalline cubic and hexagonal phases is described by Engström et al. (1983).

Reversed cubic liquid crystalline phases can generally be fragmented by one of the following procedures a)–d):

a) Add, to the equilibrated homogeneous cubic or intermediate phase, an aqueous solution, not necessarily any molecular solution, of one or more amphiphilic block copolymers where the hydrophilic lipophilic balance (HLB) of the block copolymer is higher than 15. Subsequent stirring with the appropriate equipment results in a coarse dispersion of fragmented cubic phase which can be aftertreated as described below. Fragmentation agents belonging to this group are certain poloxamers, such as poloxamer 407 and poloxamer 188 (Lundsted and Schmolka 1976a, Lundsted and Schmolka 1976b, Schmolka 1969) and certain amphiphilic proteins, such as casein.

Examples of other surface active polymers that can potentially be used as fragmentation or stabilization agents, either alone or in mixtures with the above, are glycoproteins as mucins and polysaccharides as alginate, propylene glycol alginate, gum arabic, xanthan, carragenan, polyvinylpyrrolidone (PVP) and carboxymethyl-cellulose.

b) Add, to the equilibrated homogeneous reversed liquid crystalline phase, an aqueous dispersion of a mixture of one or more amphiphilic block copolymers, such as in procedure b), and lipids, such as phospholipids, preferably such mixtures of phospholipids. The ratio of lipid to polymer should not be greater than required to maintain or establish the liquid crystalline phase constituting the interior according to above.

c) Fragment the homogeneous cubic phase by means of ultrasonic devices under controlled conditions in a solution of amphiphilic substance(s), again generally of HLB 15 or more. Procedure c) can also be used in conjunction with procedures a) and b) to shorten processing times.

d) Co-equilibrate the starting material, at elevated temperature, with an amphiphilic substance that forms a cubic or intermediate phase at the equilibration temperature and one of the following structures at the temperature desired for the formulation (typically 37° C., physiologic temperature): 1) a lamellar structure; 2) a lamellar crystalline structure; 3) an L3 phase. The fragmentation procedure is brought about through rapid cooling of the system in which one of the structures 1–3 is formed at well-defined crystallographic planes in the cubic phase or at defects in the cubic phase. Examples of substances which can be potentially used for the introduction of particular surface phases include: class 1) phosphatidylcholines such as phosphatidylethanolamine and ester derivatives thereof, phosphatidylinositol, phosphatidylglycercol, cationonic surfactants, such as didodeceyldimethyl ammonium bromide (DDAB), monoglycerides, all of which form lamellar phases in equilibrium with the interior phase and with excess of solution; class 2) monoglycerides forming a lamellar crystalline phase in equilibrium with the cubic and excess solution phase; class 3) In addition to those given in procedure a) above phosphatidylglycerols and phosphatidylethanolamine, both with chain lengths of 18 carbons or above and unsaturated, can be mentioned. Repeated freeze-thawing cycles can be used to control particle size distribution, and the dispersion obtained can be aftertreated as described below.

All except procedure d) take place above the main transition temperature of the lipid bilayer or lipid mono-layer constituting the interior phase. Any variation of the procedures a)–d) which utilizes the nature of the exact potentials, i.e. uses another pathway so to achieve substantially the same result as disclosed herein, fall within the scope of the current invention.

3.1.1. Examples of procedures a) and b)

Materials: A GMO prepared by molecular distillation was purchased from Grindsted Products A/S, glycerol monooleate (GMO) (85-06) (074832-FF 8-009), (Braband, Denmark), and consisted of 98.8% monoglycerides, 1.0% glycerol, 1.0% diglycerides and 1.0% free fatty acids. The fatty acid composition was C16:0:0.5, C18:0:2.0, C18:1:92.3, C18:2:4.3, C18:3:trace, C20:4:0.5 wt. %, as stated by the supplier. Purified poloxamer 407, also name, Pluronic F-127, was obtained from BASF Corporation (Wyan-dotte, USA). Soybean phosphatidylcholine (SPC) was purchased from Lucas Meyr (Epikuron 200) with a fatty acid pattern according to Rydhag (1979) of: C8:0.8, C12:2:12.2. C16:1:0.4, C18:2.7, C18:1:10.7, C18:2:67.2 and C18:3:6.0. Double distilled water was used in all experiments.

In the ternary phase diagram of the GMO/poloxamer 407/ water system the solubility of the fragmentation agent, in this case poloxamer 407, in the cubic phase originating from the binary GMO/water system is such that it introduces the formation of a new cubic phase which is in equilibrium with an L3 phase which exists between 78–90 wt. % of water and an aqueous phase. These three phases form the boundary of the constituents of the invention in this particular system, by the three phase region where the interior phase, the surface phase, and the solvent-rich solution phase coexist. Thus only one particular cubic phase, a cubic phase $Q^{229}$ with a lattice parameter of 15 nm and a composition of 50/3.5/46.5 wt. % of GMO/poloxamer 407/ water, respectively, is fragmented by means of the introduction of disclinations caused by the local formation of the dispersable phase, the L3 phase, whose composition is 6.5/4/89.5 wt. % of GMO/poloxamer 407/ water, respectively. Mixtures of the compounds whose composition is such as it falls within the boundaries of the three phase region are readily fragmented, even spontaneously with some fragmentation agents acting by this mechanism. Such mixtures thus fall within the scope of the current invention.

The following procedures have routinely been used to produce the particles of the invention: Typically an aqueous poloxamer 407 solution was added to a homogeneous cubic phase GMO/water (65/35 w/w %). The amount of poloxamer 407 solution can be varied within the three phase region described, i.e., in the approximative range of 0.8–3.5 wt. % of poloxamer 407. When necessary, the mixture was stirred on a magnetic stirrer until the cubic phase had fragmented into particles with the desired properties, such as size and adhesiveness. Typically water was added to a powdered GMO in the ratio 65/35 w/w %. The mixture was then equilibrated at room temperature for some hours until a clear isotropic phase was obtained, after which an aqueous poloxamer 407 solution was added according to concentrations given above.

Analogous behavior of the GMO/poloxamer 407/ water system is obtained if the poloxamer is changed to poloxamer 188 (Pluronic F68) instead of 407. In the GMO/poloxamer 188/ water system the three phase region in which the cubic phase constituting the interior of the current invention has the composition 53/4/43 wt. % of GMO/poloxamer 188/ water and the L3 phase constituting the dispersable, or surface phase has the composition 10/18/72 of GMO/poloxamer 188/ water. The three phase region in which the particles of the current invention can be produced is thus defined.

The fragmentation procedure itself, in these and the other systems presented, requires very little input of energy, and fragments of the interior phase are spontaneously formed by simply mixing the components. In all systems homogenizing devices, e.g., valve homogenizers can be used as described below.

The addition of any kind of compound which does not cause any unfavorable phase change (unfavorable in the sense that none of the herein disclosed interior phases is formed) behaves analogously to the systems described, and it is only the extension and location of the three phase region which is changed, due to shifts in the phase boundaries, of the phase regions constituting the interior phase as well as the surface phase. For example, the system of GMO/soybean lecithin (SPC)poloxamer 407/ water is found to behave analogously to the GMO/poloxamer 407/ water and GMO/poloxamer 188/ water systems. The same analogy holds for a variety of other compounds as well, exemplified by somatostatin and insulin as described below.

In addition to the above systems the inventors found the formation of the current particles in: the GMO/DDAB/water system, with less than 3 wt. % of DDAB, in which particles with an interior phase of cubic phase and an exterior of L3 phase are formed; systems of dioleoylphosphatidylethanolamine (DOPE) in combination with DDAB and or GMO, as well as diacylglycerides such as diolein.

3.1.2. Structure of the dispersion formed according to procedures a) and b): Evidence for an intraparticle cubic phase The strategy in the structural evaluation of cubic phase dispersions prepared according to procedure a) has been to use a combination of the following: i) phase diagram studies; ii) detailed SAX diffraction studies to complement the phase diagram studies and to verify directly the existence of cubic phases; iii) visualization of the dispersed structure by detailed light microscopy and electron microscopy (EM) studies; iv) 31P-NMR to warily the existence of isotropic signals in the dispersions, indicative of cubic or L3 phases; v) light scattering studies for the measurement of particle size distributions. All steps in the evaluation procedure have been performed on homogeneous phases and on non-homogenized and homogenized dispersions, with the exception of EM which was not applied in the case of homogeneous phase studies. The results are summarized below.

3.1.2.1. The GMO/poloxamer 407 and poloxamer 188 and GMO/SPC/poloxamer 407-water systems From X-ray studies of the fine structure of the cubic phase swelled with poloxamer the inventors have shown that it is built up of a bilayer similar to the cubic phases in the GMO-water system but in which the PPO-units of the poloxamer 407 are located in the bilyaer close to the apolar/polar interface with the PEO-units in the aqueous labyrinths. From this it is concluded that the observed decrease in the bilayer curvature of the cubic phases appears to be an effect of the PPO-units rather than the PEO-units. It is further proposed that the formation of the colloidal fragmented dispersions of the cubic phase is an ultimate consequence of the proposed fine structure and its relation to the formation of an L3 phase. Thus, the inventors have shown that the formation of the L3 phase which is governed by, among other things, a melting of the lattice structure and a simultaneous approximately two-fold increase of the characteristic length scale along a cubic/L3 tieline. This leads to a weakening of the interbilayer forces and a subsequent loss of long-range order. This is utilized in the current invention, in such a way that the formation of the L3 phase acts very similar to an explosive, in that it bursts the homgoneous cubic phase. The pathway for the explosive force is the formation of the L3 phase, which takes place along the most cost-effective energy-minimized path. A particle will, however, not separate from the homogeneous cubic phase until the whole of its boundary is covered with L3 phase. This can very dramatically and readily be visualized in the polarizing microscope, in which the fragmentation procedure can be seen to take place under the formation of small streaks of birefringence along the cracks of the homogeneous cubic phase in an otherwise totally isotropic picture. Sometimes, fragments are sticked to the homogeneous cubic phase which indicates that the surface is not fully covered with L3 phase.

The phase diagram of the GMO/poloxamer 407/ water system is dominated by an extended cubic phase region ranging from 18 wt. % to about 67 wt. % water and with a maximum content of 20 wt. % poloxamer 407. At higher concentrations of the poloxamer 407 the cubic phase "melts" into an isotropic L2 phase. The system exhibits four other one phase regions, one of which appears in the diluted region, in between a diluted lamellar phase and the cubic phase, viz an L3 phase. Its structure has been shown by the inventors to be the same as for the L3 phases frequently found in surfactant-water system (see 2.5.2).

Four cubic one-phase regions were verified experimentally by the existence of the necessary two-phase samples with clearly separated, subsequently identified cubic phases, and the existence of the necessary multiple-phase samples formed with the adjacent phase regions. The type of the cubic phases may be assumed to be of type II based on their location in the phase diagram. By means of SAXS the cubic phase which participate in the three phase region where fragmentation takes place can be determined. The same principle phase behavior is found in the GMO/poloxamer 188/ water and in the GMO/SPC/poloxamer 407/ water systems, and the existence of a three phase region where the interior phase (cubic) and the surface phase (L3) coexist with an excess of water. In addition we have studied the phase behavior of the GMO/poloxamer 188/ water at increased temperature to check for the critical temperature when this three phase region disappears. No such temperature was found and the three phase region existed at least up to 60° C. which was the highest temperature studied. A general decrease of the extension of the cubic phase was noticed to take place at high water content (low curvatures) which correlates nicely with the believe in increased entropy in the hydrophobic part of the bilayer as the temperature is increased. The most important feature for this text is the existence of The three-phase region where the L3 phase and the cubic phase are coexisting with the diluted solution and in which region the current particles may be prepared.

3.1.2.2. Phase behavior in polypeptide- and protein-water systems and their dispersions The phase behavior of the GMO-somatostatin-water system is similar to that of the MO/lysozyme/water system. Somatostatin, like most polypeptide hormones, has a very low solubility in water and tends to associate into various types of molecular aggregates. The solubility of monomeric somatostatin (molecular weight 1637.9) in aqueous solution has been estimated to be 0.3 mg/ml. Furthermore, it has a net charge of 4 and a pI=10. The phase diagram of GMO-somatostatin at 20° C., clearly shows an increase of the solubility of somatostatin when formulated in the cubic phase. The cubic phase regions extend towards the wet region meaning that the curvature of the cubic phase(s) is decreased as the amount of somatostatin is increased. This reflects the amphiphilic nature of somatostatin analogous to the case of GMO/poloxamer 188 or a maximum of 10 wt. % of somatostatin have been studied. The limit of swelling of the cubic phase is increased by nearly 10 wt. % as well. Several two-phase samples have been observed in the cubic phase region and again there exists a complicated, yet not fully resolved, cubic mesomorphism. However, as with many other hydrophilic proteins and polypeptides, we can conclude that the "average" curvature of the bilayer in the cubic phase is decreased as an effect of increased surface area of the apolar/polar interface caused by the presence of somatostatin. In line with this $Q^{229}$ phase has been observed. We have also investigated the phase behavior at 37° C., which shows the marked decrease of the extension of the cubic phase at lower curvatures, i.e. higher amount of water. Again analogously to the results for the GMO/poloxamer 188/ water system. As seen a clear change of the phase boundaries toward the "dry" region is obtained and this is compatible with an increased curvature as expexted.

3.1.2.3. Freeze-fracture electron microscopy study

We have also investigated the homogenized dispersions, prepared by methods a) and b) given in section 3.1. and 3.1.1. and homogenized-as described in section 3.3.1., with freeze-fracture electron microscopy (FFEM) in collaboration with W. Buchheim, Dept. of Chem. Phys., Federal Dairy Research Centre, Kiel, Germany. Representative micrographs show the characteristic pattern of a cubic phase enclosed in regular shaped particles, often with square or rectangular cross-sections. The results are revealing, showing particles with a very characteristic appearance, and the structure of cubic phase is clearly seen. The periodicity of the cubic phase can be estimated to be about 150 Å, in good agreement with the X-ray data. Furthermore, the average particle size is estimated to be 300 nm, which is in the same range as obtained by the light scattering experiment (see section 3.1.2.5.). From the largest particles (about 2 μm) a shift between adjacent fracture planes corresponding to half the periodicity could be seen, which indicates that the structure is body-centered, in agreement with the X-ray data.

The same results were obtained in the investigation of a fragmented unhomogenized somatostatin cubic phase, used in section 4.1.4.1.

3.1.2.4. $^{31}$P-NMR study

In order to investigate and further support the structural evaluation of the particles claimed an NMR investigation was performed. Dispersions were studied by 31P-NMR by means of which it is possible to differentiate between samples giving isotropic line shapes and those giving anisotropic shapes. The latter is characteristic of the lamellar and hexagonal phases, and the former of several isotropic phases, among them the cubic phase and isotropic solution phases. If the sample is a mixture of two (or more) phases, the NMR spectrum is considered to be a superposition of the individual signals (cf. Lindblom and Rilfors 1989). It is important to note that NMR is a nondestructive method in the sense that it does not need separation of the individual phases.

Both homogenized and crude dispersions as obtained by the procedures given in sections 3.1. and 3.1.1. and subsequently homogenized by the procedure outlined in 3.3.1. were used. No significant difference could be observed between the two dispersions. Representative powder-type spectrum was recorded at resonence frequencies of 40.508 MHz on a modified Varian XL-100-15 spectrometer operating in a pulsed Fourier transform mode. Only two rather closely located peaks, with an area relation of 2:1, of narrow bandshape were observed. This indicates the presence of fast isotropic motion i.e. isotropic phases. Even if it is tempting to assume that these peaks correspond to the cubic and L3 phases, it is important to stress that these peaks can arise from, e.g., an L2 phase or vesicles, i.e., unilamellar liposomes. However, together with the evidence obtained with the other methods, the presence of two such "isotropic" peaks supports the structure as deduced from the FFEM and X-ray studies.

3.1.2.5. Photon correlation spectroscopy (PCS) study

Homogenization of the coarse dispersion as described in section 3.3.1. results in a dispersion which shows enhanced colloidal stability, mainly because the reduction of particle size. Light scattering experiments (performed with a Malvern PCS100 spectrometer (Malvern Instruments Ltd., UK) equipped with an argon-ion laser and K7032-OF correlator) indicated that the mean particle size was about 200–1000 nm, depending on the pressure, number of passages and temperature during the homogenizer used in the experiments, as described in section 3.3.1. A representative size distribution of a homogenized dispersion shows the presence of very few particles bigger than 1 µm and about 90–95% of the particle size lies in the interval of 150–500 nm with a mean of about 300 nm. This is in agreement with the results obtained by FFEM (see section 3.1.2.3.).

3.2. L3 phase-dispersions

These particles have been obtained through lyctropic phase transformation of %he cubic phase dispersions described above. That is, the procedure is substantially the same, but the intention is that due to the existence of an L3 phase in equilibrium with diluted solution (knowledge of which is obtained through prior phase diagram studies), the particle interior will be an L3 phase rather than a cubic phase. Systems where an L3 phase is known to appear in equilibrium with diluted solution are ternary systems containing amphiphilic proteins, such as the casein/monoglyceride/water system, and the poloxamer 407/ monoglyceride/water and poloxamer 188/ monoglyceride/water systems. The addition of lecithin, such as SPC, egg yolk lecithin, or lamellar forming cationic surfactants such as DDAB according to the above procedures may favor the formation of these particles over the cubic phase particles, as may the increase in the concentration of the third, amphiphilic component. Thus, the production procedures are similar to those described for fragmentation of cubic phases with The exception of procedure c) in section 3.1. The L3 phase particles are composed of bicontinuous L3 phase interiors stabilized by the action of the palisades created as described in a) and b) in section 3.1.

In summary some of the most important fragmentation agents can be found within The following groups of compounds:

POLYMERS

Amphiphilic polymers:

amphiphilic block copolymers: amphiphilic di- and triblock copolymers: pluronics (polyxamers) and tetronics: poloxamer 407 (Pluronic® F127), poloxamer 188 (Pluronic® F68); polyvinylpyrrollidine (PVP) amphiphilic proteins: glycoprotein, casein lipopolysaccharides: Lipid A and derivatives, analogs to Lipid A, and derivatives thereof.

diacyl lipids with polymeric polar heads.

Amphiphiles, including lipids, and lipid-like surfactant and derivatives thereof Nonionic: polyethyleneoxide surfactants: n-alkylpolyglycol ethers ($C_iEO_j$); various derivatives of polyoxyethylene (POE): POE fatty amine, POE glycol monoethers, POE fatty ester, POE fatty alcohol; polysorbates; sorbin esters.

Anionic: alkylsulfates; soaps; sulfosuccinates.

Cationic: quaternary ammonium compounds (cationic soaps): cetyltrimethylammonium bromide (CTAB), didodecyldimethylammonium bromide (DDAB) etc.; N-[1-(2,3-dioleoyloxy)propyl]-N, N-trimethylammonium chloride (DOTMA) and various analogs; cationic headgroup derivatives of monoacyl- or diacylglycerol.

Zwitterionic: phospholipids: phosphatidyl-choline (PC), -ethanolamine (PE), -serine (PS), -glycerol (PG): dioleoylPC (DOPC), dioleoylPE (DOPE), dioleoylPG (DOPG) (All C18:1 alkyl chains, but there are many other examples and combinations); alkyl betaine derivative.

Lipid derivatives: polyethyleneglycol derivatized (phospho)lipids (PEG-PC and PEG-PE); ethoxylated cholesterol.

Glycolipids: mono-, di- and polyglycodiacylglycercls.

3.3. Aftertreatment and additional processing

Depending on the desired properties of the final formulation, selected in view of the particular application, various aftertreatment processes may be desired. Particles made according To procedure b) section 3.1. can be homogenized with preserved structure by means of suitable equipment, such as a valve homogenizer, so as to achieve a certain particle size distribution. Other processes such as sterilization by means of an autoclave, sterile filtration, or radiation techniques, or combinations thereof, may be applied with preservation of the intraparticle structure and of the physicochemical state of the active compound, as now described.

3.3.1. Homogenization

Depending on the system in which particles, as described above, have been obtained and dependent on the desired properties, the dispersion can be homogenized so as to achieve a satisfactory particle size distribution and surface properties. The decrease of particle size increases the stability of the dispersion, with regard to settling phenomena. However, it is important not to treat the destabilization processes with normal procedures for emulsion system, since the current system is not acting as such, nor can it be defined as such. The associated destabilization is treated in more detail in section 3.4.3.

After fragmentation of the cubic phase the dispersion may have different surface characteristics depending on the fragmentation agents used. This in turn affects particle size and properties such as adhesiveness, and it can be advantageous to homogenize the dispersion for reduction in particle size and a narrow particle size distribution. In particular, homogenization is important in the use of the current particles as drug delivery system.

In practice several different homogenizers may be used; however, the introduction of new equipment requires a thorough structural evaluation so as to insure that the particles still have the intraparticular properties of the cubic phase as described above. In this work we have used two principle devices to homogenize the dispersions: an ultrasonic device and a valve homogenizer. The homogenizer used is described in detail by Thornberg and Lundh (1978). Briefly it is a pneumatic continuous valve homogenizer for laboratory use equipped with a heat exchanger and a valve. Its capacity can be varied as well as its pressure, which can be monitored. Usually, batches of 10–50 ml was continuously homogenized at 25° C., with pressures applied in the range of 80–180 kBar. The dispersion was carefully investigated during and after the homogenization.

Preparation of homogenized dispersions used for FFEM, 31P-NMR, and PCS studies: A batch of the GMO/water cubic phase was prepared, sealed and stored under nitrogen atmosphere at room temperature. The water content was checked by frequent ocular examination. Normally dispersions were prepared in samples of 30 ml, with a total lipid composition of 10 w/w %, and final concentrations of the GMO/SPC/poloxamer 407 system of 6.5/3.5/1.0 w/w %, st. These dispersions were prepared with the GMO/water cubic phase as starting material for the dispersions. A suitable amount of the GMO/water (65/35 w/w %) cubic phase was weighed into a ordinary beaker and mixed with appropriate amounts of a premixed dispersion of poloxamer 407 and SPC in accordance with the final concentration. The mixture was stirred for some hours until the coarse dispersion was suitable to homogenize. The homogenization was carried out at 25° C. in continuous laboratory valve homogenizer, described in detail by Thornberg and Lundh (1978). Immediately after homogenizing the dispersions were collected in 12 ml ampoules which were filled with nitrogen and flame sealed. All dispersions were stored at room temperature.

The increase in stability is indicated by the fact that ultracentrifugation at 250,000 xg (20° C., 24 hr) was not enough to separate the pases satisfactorily as compared to 40,000 xg (20° C., 24 hr), at which a coarse dispersion of a corresponding sample was separated. By examination of samples after each passage through, the valve, both in the microscope and by X-ray experiments, performed after separation of the dispersion by means of an ultracentrifuge, it was deduced that no apparent changes of the structure, other than size reduction, had occured.

All the steps of the dispersion procedure were carefully followed by ocular inspection and by light microscopy observations, looking for signs of birefringence and estimations of the particle size. The stability of the dispersions was judged by ocular inspection.

3.3.2. Sterilization

Due to the stablization by the fragmentation agent, the sterilization method has to be carefully established for each system under investigation. Particles of the cubic phase dispersion type stabilized with poloxamers according to above might, however, be sterilized by several methods without affecting the final structure or the physical properties of the particles. This is due to the very high inversion temperature and the very high cloud point temperature (or lack thereof) for these amphiphilic block copolymers. Similar properties can be found to be valid for other block copolymers listed as fragmentation agents above. Thus, these formulations can be sterilized by autoclaving techniques with the consideration of peroxidation carefully evaluated and taken into account.

For the majority of dispersed systems sterile filtration is the only currently acceptable method available. Techniques such as those suggested and currenctly used in the field of biotechnology, in particular liposome and emulsion technologies can be used in connection with the current invention.

3.3.3. Further stabilization

Destabilization procedures due to the colloidal nature of the current particles may in principle be avoided by the same methods used in other colloidal systems, such as emulsion and dispersion technology. In particular, addition of polymers such as alginates, amylopectin and dextran, may enhance stability, as well as the use of steric stabililizing fragmentation agents.

3.3.4. Freeze drying

Protein cubic phases can be freeze dried with retained protein structure (enzyme activity) after reconstitution (Ericsson 1986). Thus, disclosed structures as reported here can also be freeze-dried and reconstituted. Such preliminary results have been performed and X-ray diffraction data show no significant difference between the original dispersion and the reconstituted dispersion. In particular, such procedures as freeze drying can be performed with cubic phases containing substantillay amounts of sugars, such as (S öderberg 1990) which is thought to protect the tertiary structure of proteins and possible other compounds as nucleotides.

3.4. Variations of methods of preparation

Formulations such as those exemplified above in general may have to be modified and processed in such ways that formulations fulfil the criteria set by the government. In particular, additives, such as glycerol, sucrose, phosphate buffers and saline in relevant concentrations, to the aqueous compartment or formulations thereof can be added wihtout changing the principle structure of the particles.

A particular feature of the dispersion made by method a) section 3.1. is that it is stable with the same principle intraparticle structure within a pH range of approximately 2–9. Similar pH stability ranges can be expected for other non ionic systems. The addition of charged lipid species, or active ionic compounds, in the formulation can thus be used as a pH sensitive releasing/triggered system.

3.4.1. Solvent-based methods

The processes described in sections 3.1. and 3.2. can be varied according to the following: by solvent solubilization of the components corresponding to the constitution of the cubic phase as described in 3.1 and 3.2 or such solubilizate plus bioactive agents as described in setion 4, or such solubilizate with or without bioactive component plus fragmentation agent as described in sections 3.1 and 3.2. Solvents that can be used are, DMSO, carbontetrachloride, ethanol, methanol, hexane, or mixtures thereof. After subsequent evaporation of the solvent a cubic phase is formed.

Evaporation can be achieved by conventional methods such as a rotavapor. Similar methods currently in use in the field of liposome preparation technology can in principle be applied to the current invention. The cubic phases are subsequently treated as described in section 3.1. for the formation of the dispersions through fragmentation of the phase constituting the interior phase, or section 3.2. for the formation of the L3 phase dispersion.

3.4.2. Dispersions with polymerizable lipids or lipid-like surfactant

Another possibility that lies within the scope of this invention is afforded by cubic phase-forming surfactants, lipids, and amphiphilic monomers that can be polymerized. In particular, those techniques which are disclosed in the following Anderson documents, concerning the polymerization of cubic and other reversed liquid crystalline phases, are in principle applicable to the present invention for the establishment of a polymrized interior phase, surface phase, or both: Anderson, D.M. (1990) Coll. de Phys. 51(23) C7-1. Anderson, D.M. and Ström, P. (1991) Physica A 176, p. 151; Anderson, D. and Ström, P. (1989 in Polymer association structures: microemulsions and liquid crystals (El-Nokaly, M.A. ed.) pp. 204, American Chemical Society, Wash. Ström, P. and Anderson, D.M. (1992) Langmuir 8, 691.

Research has recently arisen in the literature as to polymerizable lipids that polymerize through peptide bonds. Cubic phase particles made and polymerized with such lipids could be processed in particular depolymerized —through polypeptide degradation and biosynthesis pathways in the body. In this way, sites of excessive or abnormal polypeptide metabolism could be targeted.

The use of polymerizable (or polymerizable/depolymerizable) compounds as dispersing agents opens up the possibility to tailor the characteristics of the palisade layer, substantially independently of those of the interior. In particular, with minimal effect on the cost effective, protein stability, and microstructure of the interior of the particles, the hydrophilic palisade could be polymerized with a resulting strong effect on the stability and molecular recognition properties of the particles. The release rate, and even the functional form of the profile, could be tailored in this same way, especially through the use of mixtures of polymerizable and non-polymerizing agents or agents with variable numbers of polymerizable groups, establishing distinguishable labyrinths through polymerization of chiral and monolayer cubic phases. In addition to triply-periodic order, an additional degree of spatial order is afforded if the two solvent networks created by the surfactant film can be independently treated, in a systematic way. We have mentioned that more sophisticated applications of these materials could be made possible if this distinction were possible; that this is in principle possible, and of potential importance, is clear from the use of this property in the prolamellar body of etiolated leaves, for example (Gunning 1967, Tien 1982). In this subsection we discussed several ways in which this might be accomplished, based on previous work of this group.

As discussed in section 2.4.2, the $Q^{212}$ cubic phase structure, which has been found in the monoolein/water/cytochrome-c system, is believed to be the same as the structure of $Q^{230}$ except that the protein is segregated into one of these networks by virtue of its stereochemistry; thus the cubic phase has one aqueous network and one network filled in with inverted micelles containing proteins.

4. Applications

Especially interesting uses of the particles claimed, or as prepared by the method claimed, are those uses which are defined in the accompanying claims. These and other uses will, however, be described more in detail below.

In the area of drug delivery, the invention is particularly well suited, though not limited, to the formulation and delivery of hydrophobic and amphiphilic compounds that have limited aqueous solubility, or are subject to undesireable degradation or non-optimal presentation to the target, especially, coformulations of nucleic acids and/or proteins with compounds related to, or needed for, the uptake, introduction or transcription, or for its enhancement, of nucleic acids. In addition, the invention is in principle well suited for intracellular targeting. The invention is well suited as an adjuvant for vaccines, such as lipopolysaccharides, particularly for peptide- or carbohydrate-based antigenic compounds and in the colormulation of immunomodulators. The invention is well suited for prolonged circulation of peptidic drugs, and more particularly it increases the therapeutic index thus decreasing systemic toxicity, which is common among compounds under investigation in the treatment of cancer and in the therapy of immune disorders, such as HIV related diseases.

Thus a drug delivery system should protect the polypeptide from degradation as well as increase the half-life so to achieve longer contact times for site-specific and chronospecific delivery, both extracellular and intracellular.

4.1 Drug delivery

A major obstacle for the utilization and delivery of polypeptides and proteinaceous active agents is their formulation. The simplest form of administration of these compounds is by direct injection in hypotonic medium into the bloodstream. However, several properties of polypeptides and proteins that may impede their delivery must be taken in consideration, such as their: i) physicochemical state; ii) chemical, enzymatic and physical instability; iii) short biological half-life of circulating compound; iv) potential of provoking immunological response; v) inability to be transported from the vascular compartment to extravascular sites with efficiency; and vi) the chronicity of their biological task.

The current invention represents a novel approach that circumvents these limitations, and furthermore provides unique means by which to achieve chrono- and site-specific delivery, including delivery specifically to intracellular sites—that is, directly to the cell organelles responsible for the activation and control of biosynthetic pathways governing cell metabolism and dis-semination of genetically-derived information. The current invention is not restricted to any particular route of administration, and administration can be made by intravenous, intramuscular, intranasal, ocular, sublingual, subcutaneous, oral, rectal, vaginal, or dermal routes, or regionally such as through intraperitoneal, intraarterial, intrathecal and intravesical routes.

4.1.1. Toxicological considerations

A problem with the use of homogeneous reversed cubic phases as drug delivery system is its well documented fusogenic property and as an effect it is hemolytic. The documentation is particularly well regarding monoolein (see e.g. Cramp and Lucy, Hope and Cullis 1981 and references cited therein). On the other hand there are reports regarding antitumor activity of certain monoglycerides (Karo et al. 1969) as well as antimicrobial effects (see e.g. Yamaguchi 1977). The current particles, prepared by the methods given in section 3.1. and 3.1.1. do not show any fusogenic activity even when the phase constituting the interior is originating from the GMO/water cubic phase, as was indicated by the absence of hemolytic products in mixtures of a cubic phase dispersion and human whole blood. The apparent absence of toxic effect in the animal test discussed herein also supports this conclusion, although clearly more testing is necessary. This apparent lack of toxicity is almost certainly due to the increased hydrophilicity of this cubic phase dispersion as compared to the homogeneous cubic phase, and through steric stabilization, both provided by the hydrophilic palisade created by the surface phase.

4.1.2. Site-specific drug delivery

It has become urgent to develop more site-selective and specifically targeted drugs. In particular, the very potent and often systemic unwanted actions of peptidic drugs require efficient targeting so as to avoid the otherwise extremely high doses which can cause, e.g., immunogenic responses. Furthermore, many of the endogenous peptidic substances considered as drugs act within 1–10 nm of their site of production. Together with their variable efficiency with time of action and the fact that polypeptides are rapidly metabolized, this clearly requires specific targeting to obtain and maintain relevant dose levels. Whether this will be achieved with the use of carriers, vehicles, drug delivery systems, or the de novo synthesis of macromolecular therapeutic systems is still an open question. Site-direction in drug delivery can be obtained by using the endogeneous routes offered. These have only been partially mapped today and perhaps the most explored pathway to obtain site selectivity has been to use monoclonal antibodies. The surface phase of the particles of the current invention can in principle be tailored so as to be used in all kinds of different interactions with e.g. tissues, so as to increase the efficiency of the drug via the achievement of site-specific delivery and thus increase its therapeutic index.

4.1.3. Organ selectivity

The use of sepcific fragmentation agents in the method of the current invention to achieve specific: interactions with a set or subset of cells within one organ can e.g. be achieved through the use of different amphiphilic block copolymers, such as the poloxamers 407 and 188. It has also been shown that the biodistribution can be altered by the different surface properties obtained by the use of these polymers. Thus, as suggested by these works, the cubic or L3 dispersions can be directed towards, e.g., the bone marrow by applying different fragmentation agents as described in section 3. The use of carbohydrates or synthetically modified block copolymers as fragmentation agents can be used in the present invention to further increase the specificity. The modification of the hydrophilic polyethyleneoxide units by conjugation with specific sugar moieties can be used as one approach.

The use of lectins (Sharon and Lis 1989) offers an attractive pathway to specific interactions with targets. It has been demonstrated that membrane bound lectins mediate the binding of both cellular and intracellular glycoproteins to membranes and in this way control the trafficking of glycoproteins. It is clear that this highly conserved and specific interaction can be used the: other way around, i.e. that the glycoprotein (or only mimic thereof) is carried by the vehicle and upon recognition by the lectin interact with the target. Again the current invention offers important novel possibilites to achieve a uniform and efficient presentation and interaction with the target.

4.1.4. Delivery of polypeptides and proteins

The success of recombinant products for use as pharmaceutics will, at least in part, be dependent on progress in the formulation of these products. However, due to the great variation of these products with regard to their physicochemical properties and biological action, a their physicochemical properties and biological action, a single delivery system is very unlikely to satisfy all the desired properties. E.g. in the formulation of polypeptides it is often thought that a sustained release should increase the bioavailability; however, there are many examples where a sustained release could cause toxic or immunogenic reactions due to, e.g., cascade effects. Clearly, the dose response and the dose determination rely on several complicated issues, from the development of international standards to the more basic understanding of the biochemical action of these products, and, still more intriguing, the patient dose dependence. Depending on the time and duration of their interaction with the target, the range of effects also might be selective. Thus, chronospecificity is also to be considered, particularly in the delivery of peptide hormons or neuropeptides.

For some polypeptides a duration of their delivery and a prolongation of their biological half-life may be of relevance and increase the bioavailability and/or efficiency. Currently most formulations of polypeptides have been concerned with the rather trivial question of increasing the biological half-life upon administration. Preparations such as liposome-associated polypeptides have been used to sustain the delivery of many polypeptides through various routes, and to some extent it has been shown that the delivery of intact and bioactive polypeptides can be prolonged for days and possibly longer. However, very few of these studies have been at all concerned with the therapeutic efficiency of the delivery. This aspect will, however, determine whether products as liposomes will be of medical or commercial importance in a specific application. The numerous obstacles to the efficient delivery of polypeptides and proteins have been considered by many authors (Sternson 1987, Lee 1988, Eppstein and Longenecker 1988, Banga and Chien 1988).

Peptidic drugs comprise a broad class of pharmaceutics and the in vivo actions of these compounds, whether administered or endogenous, include a wide range of effects; due to their interactions, these are intrinsically coupled, and therefore some of the peptidic drugs are treated separately elsewhere in this text. Thus to understand and control systemic effects, site-specific delivery must be considered along with the above-mentioned considerations.

Coformulations of absorption enhancers such as bile acids, for example sodium glycocholate and deoxycholate, as nonionic polyoxyethylene ethers and derivatives of fusidic acid such as sodium taurodihydrofusidate, or a combination of these, are easily achieved with the current invention.

For some peptidic compounds precautions have to be taken to avoid precipitation, fibrillation, and/or aggregation of the compound. In the current invention such changes are most conveniently avoided by adding the peptidic compound as a solution to a preequilibriated cubic phase with the smallest possible amount of water within the cubic phase region so as to swell the cubic phase to the cubic phase considered for the final equilibration and subsequent fragmentation, or by adding the peptidic solution to a preequilibriated mixture of lamellar and cubic phase, i.e. to a two-phase region consistent with the coexistence at equilibrium conditions of lamellar phase and cubic phase in accordance with phase behavior, followed by equilibration and subsequent fragmentation. The latter is exemplified in the GMO (or MO or mixtures of monoglycerides or mixtures of certain monoglycerides and phospholipids or lecithin)/water system.

Examples of peptidic compounds which can be formulated with the current invention are: bovine serum albumin (BSA), insulin, epidermal growth factor (EGF), gonadotropin-releasing hormone, interferons (type I and II: I:alfa (15–20 different species) and beta; II: gamma), luteinizing hormone, vasopressin and derivatives, somatostatin and analogs. Other peptide-based pharmaceuticals that are active in the cadiovascular, CNS, and gastrointestinal regions, as well as those modulating the immune system or the metabolism can be formulated either alone or in mixtures by the current invention.

4.1.4.1. Example of intravenous somatostatin formulation in the rabbit

Somatostatin is an endogenous small polypeptide with a wide range of biological effects which have been subject to intensive research activity since it was discovered in 1968. The very broad spectrum of actions of somatostatin have led to an immerse search for therapeutic applications. However, because of its low biological half-life, great efforts have been put into the development of more stable and specific analogues more suitable for clinical applications.

In order to investigate the properties of cubosomes as a drug delivery system, a somatostatin loaded cubic phase dispersion preparation was studied in the rabbit using intravenous bolus injection. After injection, blood was sampled at regular intervals, and concentrations of somatostatin were determined as the specific immunoreactivity in plasma. It is important to note that these measurements do not reveal the amount released, and the amount of somatostatin measured can very well be located in the cubosomes. This is a common analytical problem shared by other drug vehicles. The result showed a significantly increased and maintained somatostatin concentration in the plasma within the time of the experiment which was six hours. Also shown is the plasma concentration after bolus injection of the peptide. From these results we can conlude that the cubosomes exhibit a prolonged circulation time. This can tentatively be explained by the palisade of PEO-units which increases the hydrophilicity. This effect has been observed for other colloidal drug carriers covered with a surface layer of poloxamer. In fact several studies have used poloxamers to prolong the circulating time of colloidal particles via an adsorption of the block copolymer to the surface of the particles, resulting in an increased hydrophilicity of the particle surface (cf. Jamshaid et al. 1988 and references).

4.1.4.2. Example of intranasal insulin formulation in the rat

Insulin (Actrapid, Novo, Denmark) has been formulated by the current invention and delivered intranasally in a rat. Insulin solution with the desired concentration was added to samples of GMO/water, corresponding to the two-phase region where the lamellar and cubic phase ($Q^{230}$) coexist, following equilibration to insure the formation of the desired cubic phase used for subsequent fragmentation. SAXS methods were used to insure that the formulation prior fragmentation corresponds to a cubic phase. Fragmentation was performed as described in section 3.1 method b) as described in detail in section 3.1.1. All steps in the formulation procedure were performed under antiseptic conditions. In the current example with regard to route of administration and the delicate properties of insulin the fragmented colloidal dispersion was chosen not to be further processed. There were no signs of instability of the dispersion during the time of the experiments (approximately 2 months).

Animal experiments were performed in collaboration with Dr. P. Ederman, Dept. of Pharmacy, Uppsala University. The formulation (10 IU/ml) was administered intranasally in rats (Wistar) and the change in the blood glucose was used as a measure of the insulin delivery through the nasal epithelia. A significant change was observed and no obvious signs of side effects were observed.

4.1.5. Adjuvant formulations and the use of the current particles as a vehicle for immunomodultative compounds The development of specific recombinant or synthetic antigenetic substances, such as subunit antigen and polypeptides, have lead to an urgent need for vaccine adjuvants since these structures are generally of low antigenicity. Therefore their promise as vaccines will rely on their formulation with adjuvants that increase cell-mediated and humoral responses (Alison and Byars 1990).

The two most often considered lipid-based colloidal vaccine adjuvants are liposomes (Allison and Gregozriadis 1974, Gregoriadis 1990) and Freunds adjuvants (Edelman 1980). Lately, however, the use of liposomes as adjuvant systems has been reconsidered and as pointed out by Weiner (Weiner 1989) liposomes do not insure an increased immune reactivity. The properties and features of some new adjuvants for vaccines have been reviewed (Eppstein et al. 1990).

It has become clear that the presentation of the antigenic structure is of great importance for the immune reactivity, response and the subsequent development of immunity and that membrane perturbations are of profound importance in immunogenic responses. Even though not generally accepted it is believed that the events upon membrane perturbations are intimately connected to the required intracellular enzyme activity and that the rationale for this is the cooperative biogenesis of intracellular membranes and especially the expression and surface properties of the plasma membrane. It is therefore very interesting to note that the biological active part of different lipopolysaccharides (LPS), Lipid A, forms a cubic phase in excess of physiological solution at physiological conditions (Brandenburg et al. 1990) and thus behaves very similar to the monoolein-water system. It can also be fragmented by the methods given in section 3 and used either alone or with solubilized vaccines and/or other immunomodulating compounds. Lidid A and synthetic analogous have frequently been used in adjuvant formulations for immunostimulation. It is therefore to be considered that coformulations of monoolein-lipid A forming a cubic phase in excess of solution would elicit strong immunogenic response. Other coformulations either with GMO, Lipid A or a combination of these, are with saponins (Barla et al 1979), bile acids (Lindström et al. 1981, Svärd et al. 1988), phospholipids (Gutman et al. 1984) and diacylglycerols.

In particular, the particles of the current invention are suitable as an adjuvant for polysaccharide antigens. It is well established that adjuvants, such as LPS's and muramyl dipeptide (MDP), induce the production—by accessory cells—of mediators, such as interleukin-1 (IL-1) and other lymphocyte growth factors, stimulating the proliferation of helper T-lymphocytes. The importance of the targeting of antigens to highly efficient presenting cells, such as interdigitating and follicular dendritic cells, has been emphasized (Allison and Byars 1986). Thus, procedures that facilitate the migration of antigens to the paracortical areas of lymph nodes, in the immediate vicinity of interdigitating cells, should favor cell-mediated immunity.

The particles of the current invention could thus be transferred to precursors of interdigitating cells at the site of injection, in afferent lymph or in lymph node sinuses.

Similarly, any procedure, such as selective receptor targeting directed towards C3b receptors on B-lymphocytes, that facilitates localization of antigens on follicular dendritic cells should increase B-lymphocyte responses.

Therapeutics which have been investigated as differentiating or inhibiting compounds are very attractive candidates to formulate by the current invention. In particular, peptidic drugs such as oligopeptides may act in the inhibition of EGF receptor. Similar approaches are currently investigated in the treatment of the acquired immunodeficiency syndrome (AIDS), a subject dealt with in section 4.1.7.1. Another potential application is the coformulation of the antigen and/or immunomodulator with cytostatic drugs such as methotrexate, so as to potentiate the immunogenic response and/or decrease or diminish potential immune responses to antigens in antibody-targeted applications of the current invention.

4.1.6. Cancer therapy

The current invention should be applicable to the field of cancer therapy. As to further details in this context reference is made to the use of liposomes for such purposes (see e.g. Weinstein 1987).

Preferential delivery to tumors is a challenge that, if solved, would represent an enormous advanve in cancer therapy. Reduced systemic concentrations of the drug being delivered is a step is this direction, and by applying the methods described in section 4.1.2. and 4.1.3, site selectivity could in principle be realized. Lipid biogenesis and the role of lipids as second messengers in the development of cancer has drawn increased research interest and activity. Coformulations of anticancer drugs and such second messengers can easily be accomplished by the current invention.

The rationale for use of lipid-based vehicles in general, and the current invention in particular, as carriers in chemotherapy is based on the following basic concept: prolonged circulation as compared to the free drug; protection and stabilization of the drug; circumvention of certain cell membrane barriers; amplification of the drug effect due to targeted drug delivery. Agents of particular interest in this connection are: doxorubicin; taxol; alopacia; cisplarin derivatives; and vincristine.

4.1.7. Antimicrobial therapy

The potency of drugs used against microbial infections, i.e. bacterial/rickettsial, parasitic and vital infections, can be correlated with their lipophilicity. The more lipophilic the more potent. Thus, the current system can solubilize large amounts of potent antimicrobial agents and at the same time protect or minimize the host from systemic toxic effects.

Many of the new antimicrobial drugs under consideration are of proteinaceous type. Some of these polypeptidic drugs considered fall also in the category of immunomodulators, such as some interferons. Further examples in this category are lymphokines for the treatment of visceral leishmaniasis, and cytokines; ampicillin for the treatment of intracellular liver and spleen infections caused by Listeria monocytogenesis; amphotericin B in the treatment of mycotic infections; ribavirin for the treatment of fever virus infecton; streptomycin for the treatment of tubercolosis and splenic infections; sisomycin for the treatment of lung infections; gentamicin for the treatment of intraperitoneal infection; and penicillin G for the treatment of intraperitoneal extracellular infection caused by Staphylococcus aureus. Applications where sustained release are of particular interest are in the treatment of genital papilloma virus infections. Coformulations of lipophilic, amphiphilic and hydrophilic antimicrobial drugs can be achieved with the current invention. Such formulations find their application in the treatment of patients of systemic microbial infections, which often is the case for patients having AIDS.

4.1.7.1. Therapy of human immunodeficiency virus-related disease

The potential for the use of the present particles in a delivery system for therapeutic intervention in therapy of human immunodeficiency virus (HIV)—related disease, especially acquired immunodeficiency disease (AIDS), follows from their potential in polypeptide and protein delivery, in the delivery of immunomodulative compounds, and in intracellular targeting and delivery of such compounds, as discussed herein. Of particular importance in this respect is their potential use in the modulation of lipid biogenesis and the subsequent membrane formation, as target for the treatment of, e.g., cancer and other hyperactive cells such as virus-infected cells.

Selective drug delivery is importance to cells which are infected or to cells which are known to be targets for HIV infection, such as CD4+T cells, certain types of B cells, monocytes/macrophages, dendritic cells, Langerhans cells, and some brain glial cells, as well as HIV infects CD8+T cells, muscle cells, fibroblastoid cells, and some neuronal cells in vitro. Thus, all these, and other, cell types are potential targets for the current particles. Indeed, the same rationale as outlined for the targeting of immunomodulators and vaccine formulations are valid in most, in particular, the high surface area and the ability of coformulation.

The formulation of drugs or the use of fragmentation agents or part thereof which binds to target cells or preferably HIV, thus enables inhibition of gp 120 induced cytocidal effect. Such compounds are CD4 analogs and antibodies to HIV. The use of the current particles benefits such interactions needed and their prolonged circulation increases these interactions.

The (site specific) delivery of reverse transcriptase inhibitors, such as 3'azido-2'3'-dideoxythymidine (AZT) and other dideoxynucleoside analogs such as ddI, d4T and AZddu using the current nomenclature, dipyridodiazepinone derivatives and tetrahydro-imidazo[4,5,1-j,k][1,4]-benzo-diazepin-2(1H)-one (TIBO) and -thione(tibo) and derivatives.

The (site specific) delivery of specific inhibitors of HIV ribonuclease H (RNase H) activity, inhibitors of transcription and translation of the virus encoded replication.

Formulations with compounds that block the processing of the virus envelop glycoprotein gp 120 and/or gp 41 or their precursor, such as N-butyl-nojirymycin.

Coformulations of certain immunomodulators or inducers thereof such as interferons, in particular IFN-gamma, with other compounds used in the treatment of HIV infections.

4.1.8. Gene therapy

The rationale of gene therapy has been discussed by many authors (cf. Wilson 1986) and the field appears to have a high potential. It is very likely that the efficiency and stability of the introduced gene will depend on its specific delivery to the target cell and on intra-cellular interactions. For example, in the treatment of bone marrow cells, an extraordinarily efficient and selective delivery is required since stem cells of the bone marrow only comprise about 0.001–0.01% of the total cells. The task to be solved by the delivery system for in vivo targeting is therefore considerable. The current invention offers not only a very high solubility of DNA fragments and/or plasmids but also protects DNA from undesireable interactions with body fluids.

4.2. Biotechnological and biomedical applications,

The considerable direct, and indirect, evidence for the high enzymatic activity in the cubic phase particles of this invention, together with their versatility in the immobilization of enzymes at high loadings make the current invention advantageous as compared to current available immobilization units in biotechnology. This has been discussed in the case of homogeneous cubic phases by Anderson (1987), and the current invention represents an improvement of that invention because of the much higher surface/volume ratio in submicron particles of the cubic phase, thus facilitating access into and out of active sites. The use of lipid-based vehicles in imaging, in particular liposomes as contrast-enhancing agents or in diagnostic nuclear medicine have been reviewed (Weinstein 1987, Caride 1985). Applications of the current particles in diagnostic imaging are as carriers of radiological contrast agents.

Delivery of oxygen can be achieved by the preparation of an oxygen carrier, such as the heme group in hemoglobulin or similar protein, in a cubic phase. Cubic phases in the system hemoglobulin-GMO-water have been investigated and are formed with high amounts of protein (>5 wt. %). Such a system can be used as blood substitute and in connection with radiation therapy of cancer. The use of polymerizable lipids, in such systems as described above could be used to enhance stability and shelf-life.

4.2.1. Transfection technology

The present invention should also be useful in the fields of transfection technology, i.e. the introduction of foreign nucleic acids into cell types/lines. Particularly, in view of the currently used liposomal system for the use in this field, such as DOPE which is a prominent non-lamellar forming lipids in aqueous systems, and the fact found by the inventors that the current particles can be formed in the GMO/DDAB/ water system (see section 3.1.1.).

4.2.2. Cell culture

The invention should also be useful in the field of cell culture, especially use of the particles as carriers of nutrients, such as amino acids, cholesterol, unsaturated fatty acids, but also as delivery systems for more sepcific proteins as immunomodulators, growth factors etc., or for the use as diagnostics, biosensor, in immuno-assays in cell culture. Also in the field of cell hybridoma technology applications are possible.

4.3. Other applications

The present invention should also be applicable to other areas, in particular applications in the area of biosensors and as catalytic particles or carriers of catalysts. Other biomedical and biotechnological areas include enzyme therapy (as with superoxide dismutase), dispersions with magnetic properties, immobilization of the particles in gel matrices. These particles can also provide sites for mineralization and crysatallization. Mineralization of a substantial portion of the porespace or porewall surface could create microporous particles with high chemical and thermal stability, and the use of conducting or piezoelectric minerals or crystals could be important. The presence of polar groups at the porewall surface makes these particles particularly well suited for mineralization.

The present invention will also find cosmetic applications. Indeed examples of the molecular constituents of the particles such as monoglycerides and poloxamers are frequently encountered in cosmetic preparations.

A curious phenomena found by the inventors is the capability of certain cubic phases, such as those formed in the GMO/poloxamer/water systems described above, to host fungi and also supply needs for their growth. Perhaps, most surprisingly the cubic phase maintains its characteristics up to several months before phase transformation takes place. Thus the fungi grow inside the cubic phase without perturbing its structure. Therefore, the current particles could be utilized as culture media/machinery for the controlled culture of single, or multiple microorganisms.

5. References Allison, A.C. and Byars, N.E. (1986) J. Immunol. Methods, 95, 157. Allison, A.C. and Byars, N.E. (1990) in New generation vaccines (Woodrow, G.C. and Levine, M.M. eds.) pp. 129–140, Marcel Dekker, N.Y. Allison, A.C. and Gregoriadis, G. (1974) Nature, 252, 252. Alving, C.R. (1987) in Liposomes from biophysics to therapeutics (Ostro, M.J. ed.) pp. 195–218, Marcel Dekker, N.Y. Anderson, D.M. (1987) U.S. patent application Ser. No. 07/052,713; EPO Appl. 88304625.2; Japanese Appl. 63-122193; U.S. patent application Ser. No. 07/500,213 (1990). Anderson, D., Wennerström, H. and Olsson, U. (1989) J. Phys. Chem. 93,4243. Banga, A.K. and Chien, Y.W. (1988) Int. J. Pharmac. 48, 15. Barla, P., Larsson, K., Ljusberg-Wahren, Norin, T. and Roberts, K (1979) J. Sci. Food. Agric. 30, 864. BASF (1989) "Performance chemcials FDA and EPA status information bulletin", Parsippany, USA. Benton, W.J. and Miller, C.A. (1983) J. Chem. Phys. 73, 4981. Bergenståhl, B. and Fontell, K. (1983) Prog. Colloid Polym. Sci. 68, 48. Brandenburg, K., Koch, M.H.J. and Seydel, U. (1990) J. Str. Biol. 105, 11. Burrows, R., Artwood, D. and Collett, J.H. (1990) J. Pharm. Pharmacol. 42, suppl. Science proceeding 127th meeting of the British Pharmaceutical conference 1990, Abstract 3P. Byars, N.E. and Allison, A.C. (1987) Vaccine, 5,223. Caffrey, M. (1989) Biophys. J. 55, 47. Caride, V.J. (1985) Crit. Rev. Ther. Drug Carrier Sys. 1, 121. Cosmetic Ingredient review (CIR) (1986) J. am. Toxicol. 5, 391. Cramp, F.C. and Lucy, J.A. (1974) Exptl. Cell Res. 87, 107. Davis, S.S., Hadgraft, J. and Palin, K.J. (1983) in Encyclopedia of emulsion technology (P. Becker, ed.) Vol. 1, pp. 159, Marcel Dekker, N.Y. Dubois, M. and Zemb, T. (1991) Langmuir 7, 1352. Edelman, R. (1980) Rev. Infect. Dis. 2, 370. Ekwall, P. (1975) in Adv. Liq. Cryst. (Brown, G.H. ed.) 1, 1. Engström, S. (1990) Lipid Techn. 2, 42. Engström, S. and Engström, L. (1992) Int. J. Pharmac. 79, 113. Engström, S., Larsson, K. and Lindman, B. (1983) EPO patent 0 126 751; PCT/SE83/0041. Eppstein, D.A. and Longenecker, J.P. (1988) CRC Crib. Rev. Ther. Drug Carrier Sys. 5, 99. Eppstein, D.A., Byars, N.E. and Allison, A.C. (1990) Adv. Drug Del. Rev. 4, 233. Ericsson, B. (1986) Ph.D. Thesis, Lund University, Sweden. Ericsson, B., Eriksson, P.-O., Löfroth, J.-E. and Engström, S. (1991) in Polymeric drug and drug delivery (R.L. Dunn and M. Ottenbrite, eds.) ACS Symp. Ser. 469, Am. Chem. Soc. Ericsson, B., Larsson, K. and Fontell, K. (1983) Biochim. Biophys. Acta, 729, 23. Fontell, K. (1974) in Liquid crystals and plastic crystals (Gray, G.W. and Winsor, P.A. eds.) vol. 2, pp. 80–109, Ellis Horwood, Chichester. Fontell, K. (1978) Progr. Chem. Fats Lipids 16, 145. Fontell, K. (1981) Mol. Cryst. Liq. Cryst. 63, 59. Fontell, K. (1990) colloid and Polym. Sci. 268, 264. Gazeau, D. Bellocq, A.M. Roux, D. and Zemb, T. (1989) Europhys Lett. 9,447. Gregoriadis, G. (1988a) ed. Liposomes as drug carriers. Recent trends and progress, John Wiley, N.Y. Gregoriadis, G. (1988b) in Liposomes as drug carriers. Recent trends and progess (Gregoriadis, G. ed.), pp.3–18, John Wiley, N.Y. Gregoriadis, G. (1990) Immunol. today, 11, 89. Gregoriadis, G., Garcon, N., Senior, J. and Davis, D. (1988) in Liposomes as drug carriers. Recent trends and progress (Gregoriadis, D. Ed.), pp. 279–307, John Wiley, N.Y. Gulik, A., Luzzati, V., Rosa de, M. and Gambacorta, A. (1985) J. Mol. Biol. 182, 131. Gulik-Krzywicki, T. (1975) Biochim. biophys. Acta 415, 1. Gunning, B.E.S. and Jagoe, M.P. (1967) in Biochemistry of chloroplasts (T.W. Goodwin, ed.) vol. 2, pp. 655, London, Academic Press. Gutman, H. Arvidson, G. Fontell, K. and Lindblom G. (1984) in Surfactants in solution (Mittal, K.L. and Lindman, B. eds.) vol. 1, pp. 143–152, Plenum Press; N.Y. Hope, M.J. and Cullis, P.R. (1981) Blochim. Biophys. Acta 640, 82. Hyde, S.T., Andersson, S., Ericsson, B. and Larsson, K. (1984) Z. Kristallogr. 168, 213. Ibrahim, H-G. (1989) J. Pharm. Sci. 78, 683. Karo, A., Ando, K., Suzuki, S., Tamura, G. and Arima, K. (1969) J. Antibiotics 22, 83. Killjan, J.A. and Kruijff de, B. (1986) Chem. Phys. Lipids 40, 259. Krog, N. (1990) in Food emulsions (Larsson, K. and Friberg, S. eds.) pp. 127–180, Marcel Dekker, N.Y. Krog, N. and Larsson, K. (1983) in Encyclopedia of emulsion Technology (Becker, P. ed.) vol. 2, pp. 321–365, Marcel Dekker, N.Y. Larsson, K. (1989) J. Phys. Chem. 93, 7304. Larsson, K., Gabrielsson, K. and Lundberg, B. (1978) J. Sci. Fd. Agric. 29, 909. Lee, V.H.L. (1988) CRC Crit. Rev. Ther. Drug Carriers Sys. 5, 69. Lieberman, H.A.,Rieger, M.M. and Banker, G.S. (1989) eds. Pharmaceutical dosage forms: dispersable systems, Vol. 2, Marcel Dekker, N.Y. Lindblom, G,. Larsson, K., Johansson, L., Fontell, K. and Forsén, S. (1979) J. Am. Chem. Soc. 101, 5465. Lindblom, G. and Rilfors, L. (1989) Blochim. Biophys. Acta, 988, 221. Lindström, M., Ljusberg-Wahren, H., Larsson, K. and Borgström, B. (1981) Lipids 16, 749. Loth, H. and Euschen, A. (1990) Drug Develop. Industr. Pharm. 16, 2077. Lundsted, L.G. and Schmolka, I.R. (1976) in Block and graft copolymerization (Ceresa, R.J. ed.) vol. 2, pp. 1–112, Wiley, London. Lundsted, L.G. and Schmolka, I.R. (1976) in Block and graft copolymerization (Ceresa, R.J. ed.) vol. 2, pp. 113–272, Wiley, London. Lutton, E.S. (1965) J. Am. Oil Chem. Soc. 42, 1068. Luzzati, V. (1968) in Biological membranes (Chapman, D. ed.) vol. 1, pp. 71–123, Academic Press, N.Y. Luzzati, V., Gulik, A., Gulik-Krzywicki, T. and Tardieu, A. (1986) in Lipids and membranes. Past present and future (Op den Kamp, J.A.F. Roelofsen, B. and Wirtz, K.W.A. eds.) pp. 137–151, Elsevier, Amsterdam. Luzzati, V., Mariani, P. and Gulik-Krzywicki, T. (1987) in Physics of amphiphilic layers (Meunier, J., Langevin, D. and Boccara, N. eds.) pp. 131. Margolis, L.B. (1988) in Liposomes as drug carriers. Recent trends and progress (Gregoriadis, G. ed.), pp. 75–92, John Wiley, N.Y. Mariani, P., Luzzati, V. and Delacroix, H. (1988) J. Mol. Biol. 294, 165. Martindale the extra pharmacopoeia (1982) (Reynolds, J.E.F. ed.) Pharmaceutical Press, London. Meadows, G.G. and Pierson, H.F. (1988) in Liposomes as drug carriers. Recent trends and progess (Gregoriadis, G. ed.), pp. 461–472, John Wiley, N.Y. Milner, S.T., Cares, M.E. and Roux, D. (1990) J. Phys France 51, 2269. Morein, B. (1988) Nature 332, 287. Morre, D.J. (1989) in The pathobiology of neoplasia (Sirica, A.E. ed.) pp. 323–344, Plenum Press, N.Y. Mueller-Goymann, C.C. (1985) Pharmazeutische Z. 130, 682. Mueller-Goymann, C.C. (1987) Acta Phar. Technol. 33, 126 Mueller-Goymann, C. (1989) Acta Pharm. Nord. 1, 238. Mulley, B.A. (1974) in Emulsions and emulsion technology (K.J. Lissant, ed.) pp. 291, Marcel Dekker, N.Y. Peptide pharmaceuticals: approaches to the design of novel drugs (1991) (Ward, D.J. ed.) Elsevier, N.Y. Pharmaceutical dosage forms; disperse systems (1988) Liebermann, A,, Rieger, M.M. and Banker, S. eds.) Vol. 1 and 2, Marcel Dekker, N.Y. Porte, G., Marignan, J., Bassereau, P. and May, R.. (1988) J. Phys. France 49, 511. Rosvear, F.B. (1968) J. Soc. Cosmetic Chemists 19, 581. Rydhag, L. (1979) Fette, Seifde, Anstrichtmittel 81, 168. Sharon, N. and Lis, H. (1989) "Lectins" Chapman Hall, London. Seddon, J. (1989) Biochim. Biophys. Acta, 1031, 1. Small, D.M. (1986) "The physical chemistry of lipids" pp. 89–96, Plenum Press, N.Y. Speiser, P. (1984) in Reverse micelles. Biological and technological relevance of amphiphilic structures in apolar media (Luisi, P.L. and Straub, B.E. eds.) pp. 339–346, Plenum Press, N.Y. Sternson, L.A. (1987) in Biological approaches to the controlled delivery of drugs. Annals of the New York Academy of Sciences, vol. 507 (Juliano, R.L. ed.) pp. 19–21, New York Academy of Sciences, N.Y. Stigi, J.F. and Lowery, A. (1990) in Specialized drug delivery systems (Tyle, P. ed.) pp. 51–217, Marcel Dekker, N.Y. Strey, R., Jahn, W., Poerte, G. and Bassereau, P. (1990a) Langmuir 6, 1635. Strey, R., Schomacker, R., Roux, D., Nallet, F. and Olsson, U. (1990b) J. Chem. Soc. Faraday trans. 86, 2253 Svärd, M., Schurtenberger, P., Fontell, K., Jönsson, B. and Lindman, B. (1988) J. Phys. Chem. 92, 2261 Söderberg, I. and Ljusberg-Wahren, H. (1990) Chem. Phys. Lipids 55, 97. Therapeutic peptides and proteins. Formulation, delivery and targeting (1989) (Marshak, D. and Liu, D. eds.) Cold Spring Harbor, N.Y. Thornberg, E. and Lundh, G. (1978) J. Food Sci. 43, 1553. Tice, T.R. and Tabibi, S.E. (1992) in Treatise on controlled drug delivery (A. Kydonieus, ed.) pp. 315, Marcel Dekker, N.Y. Tiddy, G.J.T. (1980) Phys. Reports 57, 1. Tien, H.T. (1982) in Solution behavior of surfactants (Mittal, K.L. and E.J. Fendler, eds.) vol. 1, pp. 229, Plenum Press, N.Y. Tomlinson, E. (1990) in Modern pharmaceutics (Banker, G.S. and Rhodes, C.T. eds.) pp. 673–693, Marcel Dekker, N.Y. Tyle, P. (1989) in Controlled release of drugs (Rosoff, M. ed.) pp. 125, VCH Publishers, N.Y. Weiner, A.L. (1989) Adv. Drug. Del. Rev. 3, 307. Weiner, A.L. (1990a) Biopharm. 3(2), 27. Weiner, A.L. (1990b) Biopharm. 3(4), 16. Weinstein, J.N. (1987) in Liposomes from biophysics to therapeutics (Ostro, M.J. ed.) pp. 277–338, Marcel Dekker, N.Y. Wilson, G. (1986) in Site-specific drug delivery (Tomlinson, E. and Davis, S.S. ed.) pp. 149–164, John Wiley, N.Y. Yamaguchi, H. (1977) Antimicrob. Agents Chemother. 12, 16.

We claim:

1. Particles comprising
   (A) an interior phase of (1) a non-lamellar lyotropic liquid crystalline phase selected from the group consisting of a reversed cubic liquid crystalline phase and a reversed hexagonal liquid crystalline phase, or (2) a homogeneous L3 phase, or any combination thereof, and
   (B) a surface phase (1) selected from the group consisting of a lamellar crystalline phase and a lamellar liquid crystalline phase, or (2) an L3 phase, or any combination thereof
   wherein said surface phase and said interior phase are distinct.

2. Particles according to claim 1, wherein the interior phase is a reversed cubic liquid crystalline phase, a reversed hexagonal liquid crystalline phase or a mixture of reversed cubic and hexagonal liquid crystalline phase and a reversed cubic-hexagonal liquid crystalline phase and the surface phase is an L3 phase.

3. Particles according to claim 2, wherein the interior phase is a reversed cubic liquid crystalline phase and the surface phase is an L3 phase.

4. Particles according to claim 1, wherein the interior phase is a reversed cubic liquid crystalline phase, a reversed hexagonal liquid crystalline phase or a mixture of reversed cubic and hexagonal liquid crystalline phase and the surface phase is selected from the group consisting of a lamellar crystalline phase and a lamellar liquid crystalline phase.

5. Particles according to claim 1, which contain added bio-active agents, or precursors thereof.

6. Particles according to claim 5, wherein said bio-active agent, or precursor thereof, is selected from the group consisting of peptides and proteins, or protein-aceous compounds.

7. A method of preparing particles from a homogeneous liquid crystalline phase or L3 phase, which comprises forming a homogeneous, non-lamellar lyotropic liquid crystalline phase selected from the group consisting of a reversed cubic liquid crystalline phase and a reversed hexagonal liquid crystalline phase, or a homogeneous L3 phase, or any combination thereof, creating a local dispersible phase, within said homogeneous phase, of a phase selected from the group consisting of a lamellar crystalline phase and a lamellar liquid crystalline phase, or an L3 phase, or any combination thereof, in the presence of a solvent phase, said solvent being of a nature with which said homogeneous phase can coexist and wherein said dispersible phase can be dispersed, and fragmentating said homogeneous phase so as to form particles, the interior phase of which comprises said homogeneous phase and the surface phase of which comprises said dispersible phase.

8. The method according to claim 7, wherein the local dispersible phase is created by means of at least one fragmentation agent which is an agent of such a nature that when combined with said homogeneous phase, or those constituents which will form said homogeneous phase, it creates said dispersible phase.

9. The method according to claim 8, wherein the fragmentation agent is selected from the group consisting of lipopolysaccharides, polysaccharides, glycoproteins and proteins.

10. The method according to claim 8, wherein the fragmentation agent is selected from the group consisting of amphiphilic macromolecules and lipids.

11. The method according to claim 10, wherein the fragmentation agent is an amphiphilic polymer.

12. The method according to claim 8, wherein the fragmentation agent is selected from the following groups of amphiphilic compounds: nonionic; anionic; cationic; zwitterionic; lipids; and glycolipids.

13. The method according to claim 8, wherein the local dispersible phase is created by a procedure according to any one of the following alternatives:

a) a solution of said fragmentation agent in a polar solvent is added to said homogeneous phase;

b) a dispersion of said fragmentation agent in a polar liquid is added to said homogeneous phase; or c) said homogeneous phase is fragmentated in a solution of said fragmentation agent in a polar solvent.

14. A method according to claim 7, wherein the particles formed are after treated by means of one or more of the following procedures: homogenization, sterilization, stabilization by the addition of polymers capable of enhancing stability of colloidal systems and freeze drying.

15. The method according to claim 7, wherein at least one bioactive agent or a precursor thereof is added at any stage of the preparation of said particles.

16. Particles according to claim 1, wherein said particles are colloidal particles.

17. Particles according to claim 7, wherein said particles are colloidal particles.

18. The method according to claim 15, wherein said bioactive agent or a precursor thereof is selected from the group consisting of peptides and proteins, or proteinaceous compounds.

19. A pharmaceutical composition of matter comprising the particles according to claim 1 and a pharmaceutically acceptable carrier therefor.

20. The pharmaceutical composition of matter according to claim 1 which is in sustained release form.

21. Particles prepared according to the method of claim 7.

22. An antigen-presenting system comprising the particles according to claim 1 and a pharmaceutically acceptable carrier therefor.

23. A colloidal drug delivery system comprising nutrients for parenteral delivery of nutrition and the particles according to claim 1.

24. A method for the parenteral delivery of nutrition, said method comprising parenterally administering a colloidal drug delivery system comprising nutrients suitable for the parenteral delivery of nutrition and the particles according to claim 1 to a patient in need of such nutrition.

25. A method for the treatment of infections, said method comprising administering an effective amount of an antifungal or antimicrobial drug and the particles according to claim 1 to treat an infection in a patient in need of such treatment.

26. A method for the treatment of cancer or AIDS, said method comprising adminstering an anticancer or anti-AIDS effective amount of a drug and the particles according to claim 1 to treat cancer or AIDS in a patient in need of such treatment.

27. A method for conducting cell culture technique or an immunoassay comprising loading the particles according to claim 1 with a nutrient for cells, immunomodulators, or growth factors.

28. A method for conducting a biosensor application or using a radiation tracer, said method comprising loading the particles according to claim 1 with a radiological contrast agent.

29. The method according to claim 12, wherein said nonionic fragmentation agent is a polyethyleneoxide surfactant.

30. The method according to claim 12, wherein said cationic fragmentation agent is a quaternary ammonium compound.

31. The method according to claim 12, wherein said zwitterionic fragmentation agent is a phospholipid.

32. The method according to claim 11 wherein said amphiphilic polymer is an amphiphilic block copolymer.

33. The method according to claim 13 wherein said polar solvent is water.

34. A method for conducting an immobilization technique comprising loading an enzyme into the particles according to claim 1 as a carrier.

35. A method for growing single crystals of proteins or inorganic substances, comprising mineralizing or crystallizing pore space of the particles according to claim 1.

* * * * *

UNITED STATES PATENT AND TRADEMARK OFFICE
CERTIFICATE OF CORRECTION

PATENT NO. : 5,531,925
DATED : July 2, 1996
INVENTOR(S) : TOMAS LANDH et al.

It is certified that error appears in the above-indentified patent and that said Letters Patent is hereby corrected as shown below: On the title page:

After [87] PCT Pub. No.: WO93/06921

PCT Pub. Date: Apr. 15, 1993, please insert the following information:

--Related U.S. Application Data

[63] Continuation of Serial No. 07/771,014, abandoned.--

Signed and Sealed this

Tenth Day of December, 1996

*Attest:*

BRUCE LEHMAN

*Attesting Officer*     *Commissioner of Patents and Trademarks*